United States Patent [19]

Wilson et al.

[11] Patent Number: 4,629,586
[45] Date of Patent: Dec. 16, 1986

[54] HEXYNYL ALKANOATES AND ORGANOLEPTIC USES THEREOF

[75] Inventors: Richard A. Wilson, Westfield; Braja D. Mookherjee, Holmdel; Michael J. Zampino, North Bergen; Manfred H. Vock, Locust; Kevin P. Miller, Middletown, all of N.J.

[73] Assignee: International Flavors & Fragrances Inc., New York, N.Y.

[21] Appl. No.: 742,301

[22] Filed: Jun. 7, 1985

Related U.S. Application Data

[62] Division of Ser. No. 679,386, Dec. 7, 1984, Pat. No. 4,539,209.

[51] Int. Cl.[4] .................... A61K 7/46; C11B 9/00
[52] U.S. Cl. .................... 252/522 R; 560/261; 426/534
[58] Field of Search ............. 252/522 R; 560/261

[56] References Cited

U.S. PATENT DOCUMENTS 3,452,105  6/1969  Marbet .................... 560/261
3,781,337 12/1973  Himmle et al. ............ 560/261
3,832,369  8/1974  Shieppuils ............... 560/261
4,081,454  1/1977  Jindra et al. ............ 426/534
4,387,047  6/1983  Sundt ...................... 426/3
4,429,151  1/1984  Boden .................... 560/261
4,539,209  9/1985  Wilson et al. ........... 560/261

Primary Examiner—Werren B. Lone
Attorney, Agent, or Firm—Arthur L. Liberman

[57] ABSTRACT

Described are the hexynyl alkanoates defined according to the generic structure:

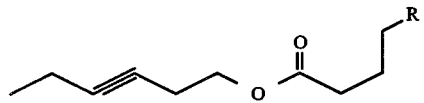

wherein R represents hydrogen or ethyl and organoleptic uses thereof in augmenting or enhancing the aroma or taste of consumable materials which are perfume compositions, colognes perfumed articles, foodstuffs, chewing gums, toothpastes and chewing tobaccos.

8 Claims, 11 Drawing Figures

GLC PROFILE FOR EXAMPLE I.
CRUDE

GC-MS SPECTRUM FOR EXAMPLE I.

NMR SPECTRUM FOR EXAMPLE I.

GC-MS SPECTRUM FOR EXAMPLE II

GLC PROFILE FOR EXAMPLE II.

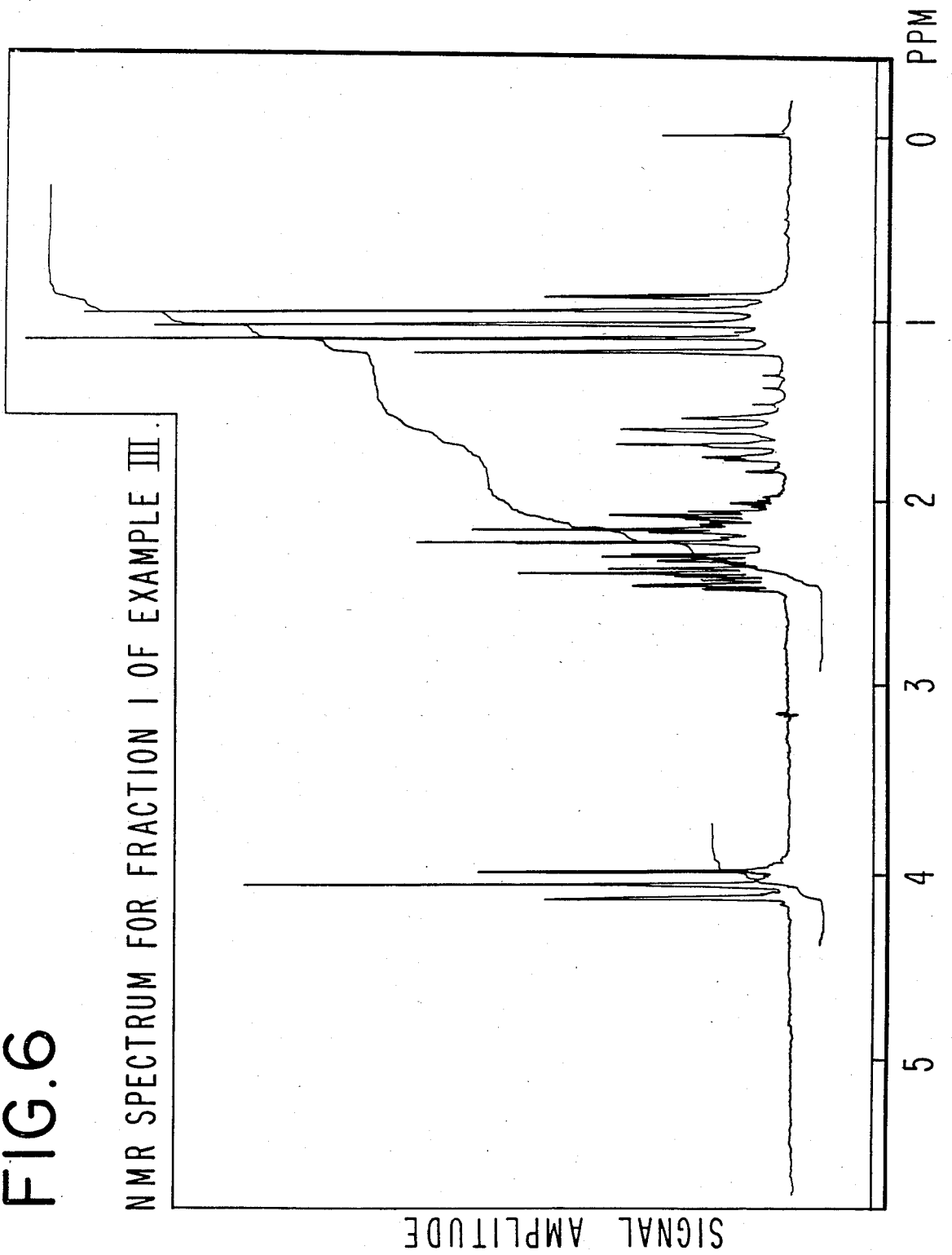
FIG. 6 NMR SPECTRUM FOR FRACTION I OF EXAMPLE III.

GLC PROFILE FOR EXAMPLE III. CRUDE

GC-MS SPECTRUM FOR EXAMPLE III.

NMR SPECTRUM FOR FRACTION 2 OF EXAMPLE III.

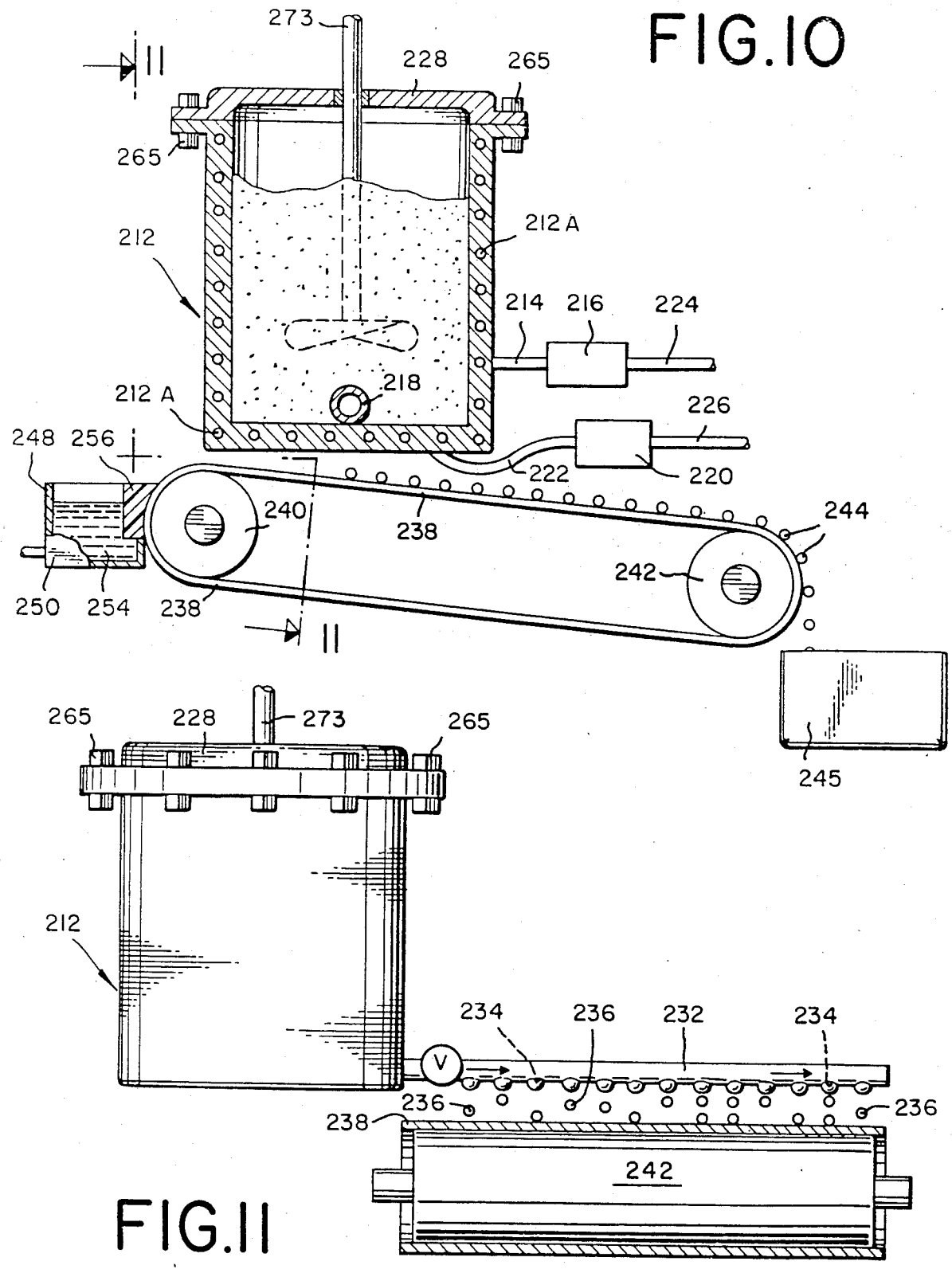

HEXYNYL ALKANOATES AND ORGANOLEPTIC USES THEREOF

This is a divisional of application Ser. No. 679,386, filed Dec. 7, 1984, now U.S. Pat. No. 4,539,209, issued on Sept. 3, 1985.

BACKGROUND OF THE INVENTION

The present invention provides hexynyl alkanoates having the structure:

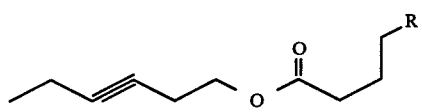

wherein R represents hydrogen or ethyl and uses thereof for their organoleptic properties in augmenting or enhancing the aroma and/or taste of consumable materials.

Materials which provide sweaty, animalic, leathery, floral, anisic, green, petitgrain, neroli and magnolia aromas with fruity, green herbaceous, floral, chamomile, orange flower and neroli topnotes are highly desirable in the art of perfumery. Many of the natural materials which provide such fragrances and contribute such desired nuances to perfumery compositions are high in cost, vary in quality from one batch to another and/or are generally subject to the usual variations of natural products.

By the same token, materials which can provide green, "Marquisa", passion fruit, sweet, fruity, brown sugar-like, and maltol-like aromas with green, "Marquisa", passion fruit-like fruity, brown sugar-like, maltol-like, maple and creamy taste profiles are highly desirable in the art of flavoring foodstuffs, chewing gums, toothpastes, medicinal products and chewing tobaccos. Many of the natural materials which provide such flavor notes and contribute such desired nuances to flavorant compositions are high in cost, vary in quality from one batch to another and/or are generally subject to the usual variations of natural products.

There is, accordingly, a continuing effort to find synthetic materials which will replace, enhance or augment the essental flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined passion-fruit flavor, for example, has been difficult and relatively costly in the areas of both natural products and synthetic products.

Artificial flavoring agents for foodstuffs have received increasing attention in recent years. For many years such food flavoring agents have been preferred over natural flavoring agents at least in part due to their diminished cost and their reproducible flavor qualities. For example, natural food flavoring agents such as extracts, concentrates and the like are often subject to wide variations due to changes in quality and type and treatment of raw materials. Such variations can be reflected in the end products and result in unfavorable flavor characteristics in said end products. Additionally, the presence of the natural product in the ultimate food may be undesirable because of increased tendency to spoil. This is particularly troublesome in food and food uses where such products as dips, soups, chips, sausages, gravies, dairy desserts and the like are apt to be stored prior to use.

The fundamental problem in creating artificial flavoring agents is that the artificial flavor to be achieved be as natural as possible. This generally proves to be a difficult task since the mechanism for flavor development in many foods, medicinal products, chewing gums and toothpastes is not completely known. This is particularly noticeable in products having passion fruit-like flavor characteristics.

Even more desirable are products which can serve as substitutes for difficult-to-obtain and natural perfumery oils and, at the same time, substitute for natural flavoring ingredients in foodstuffs, chewing gums, medicinal products, toothpastes and chewing tobaccos.

Bicchi, et al, Chem. Abstracts, Volume 98, Abstract No. 52004x (Title of paper: "Considerations And Remarks About Honey Volatile Components", "Recent Dev. Food Anal. Proc. Eur. Conf. Food Chem. 1st, 1961 (Published 1982), pages 137–42) discloses the presence in honey volatiles of 3-hexynyl acetate as well as cis-3-hexenyl butyrate having the structures, respectively:

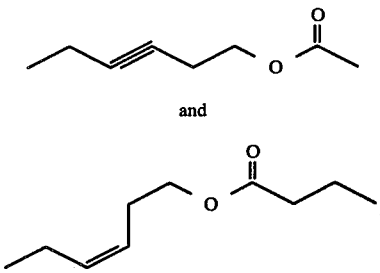

The 3-hexynyl acetate has a fruity, green aroma profile with balsamic and cinnamic topnotes. In addition, the 3-hexynyl acetate has a sweet and green aroma and taste profile at 1 ppm.

Arctander "Perfume And Flavor Chemicals (Aroma Chemicals)" published in 1969 discloses ethyl-2-heptynoate having the structure:

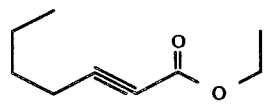

at Monograph 1261. It is described by Arctander as having a "powerful, leafy-green odor of moderate to poor tenacity". Arctander at Volume II, Monograph 2425 discloses octyl octynoate having the structure:

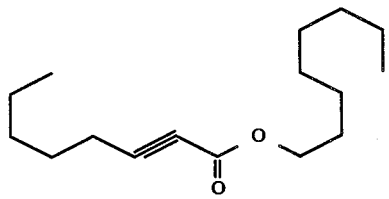

as having an "oily-green, mildly leafy and somewhat fatty odor of considerable tenacity".

3-Hexynol having the structure:

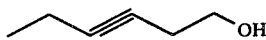

is a known compound (Environmental Protection Agency Cumulative Supplement II, Substantive Name Index CAS. No. 1002-28-4).

However, nothing in the prior art discloses the unexpected, unobvious and advantageous organoleptic properties of the compounds of our invention defined according to the structure:

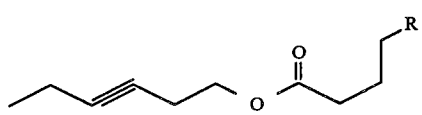

wherein R represents hydrogen or ethyl.

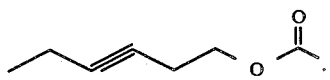

Figure 2:
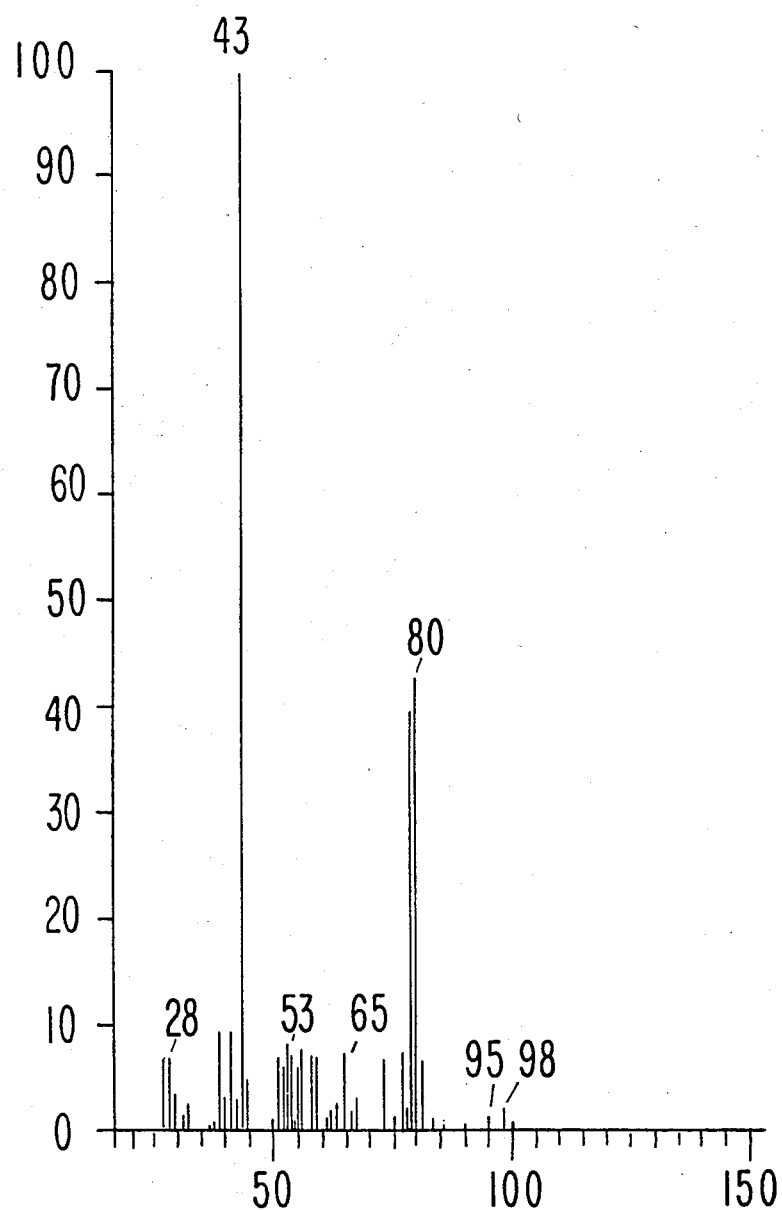

FIG. 2 is the GC-MS spectrum for the compound having the structure:

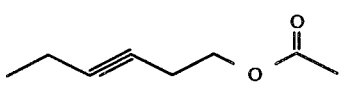

prepared according to Example I.

Figure 3:
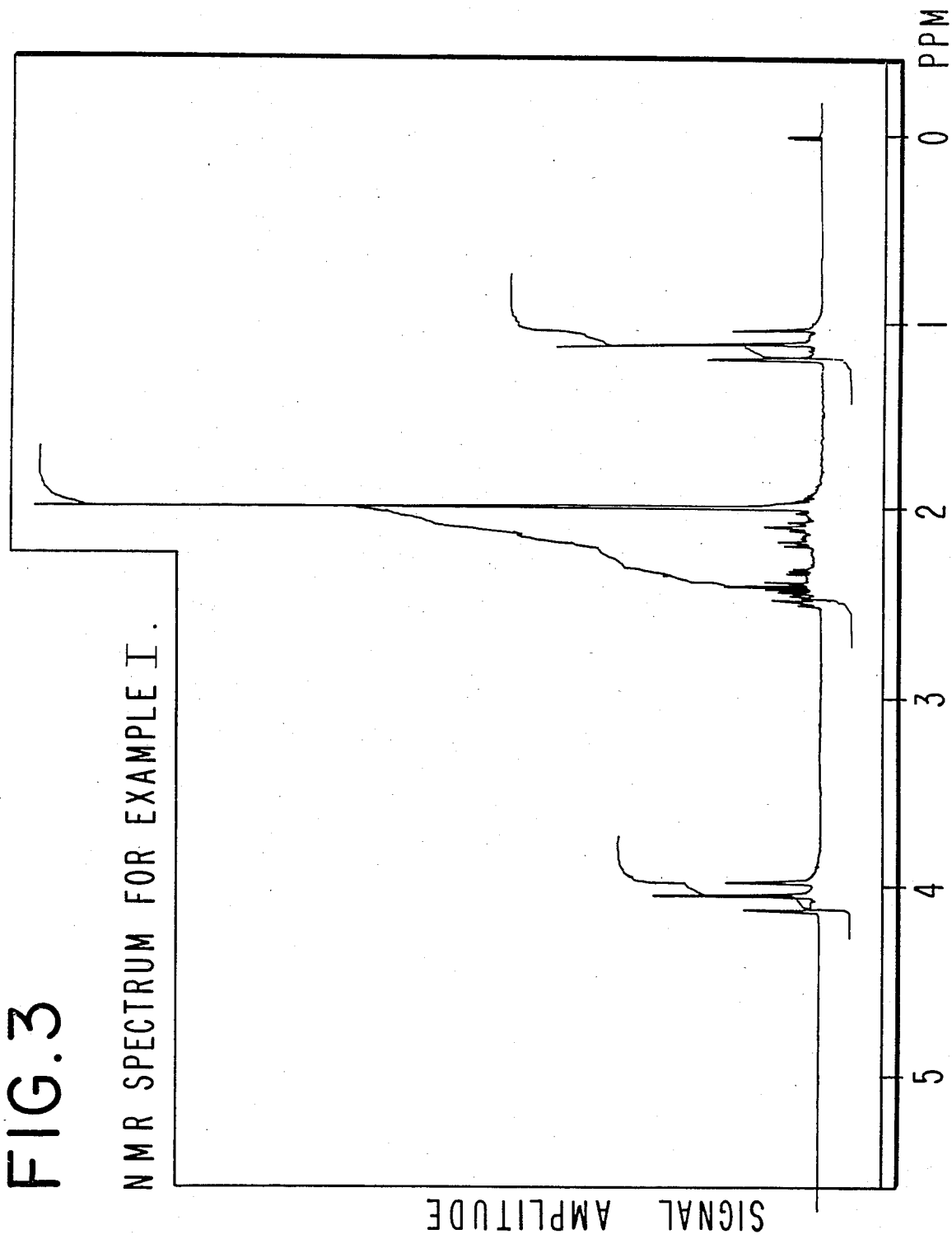

FIG. 3 is the NMR spectrum for the compound having the structure:

produced according to Example I (Conditions: Field strength: 100 MHz; Solvent: CFCl₃).

Figure 4:
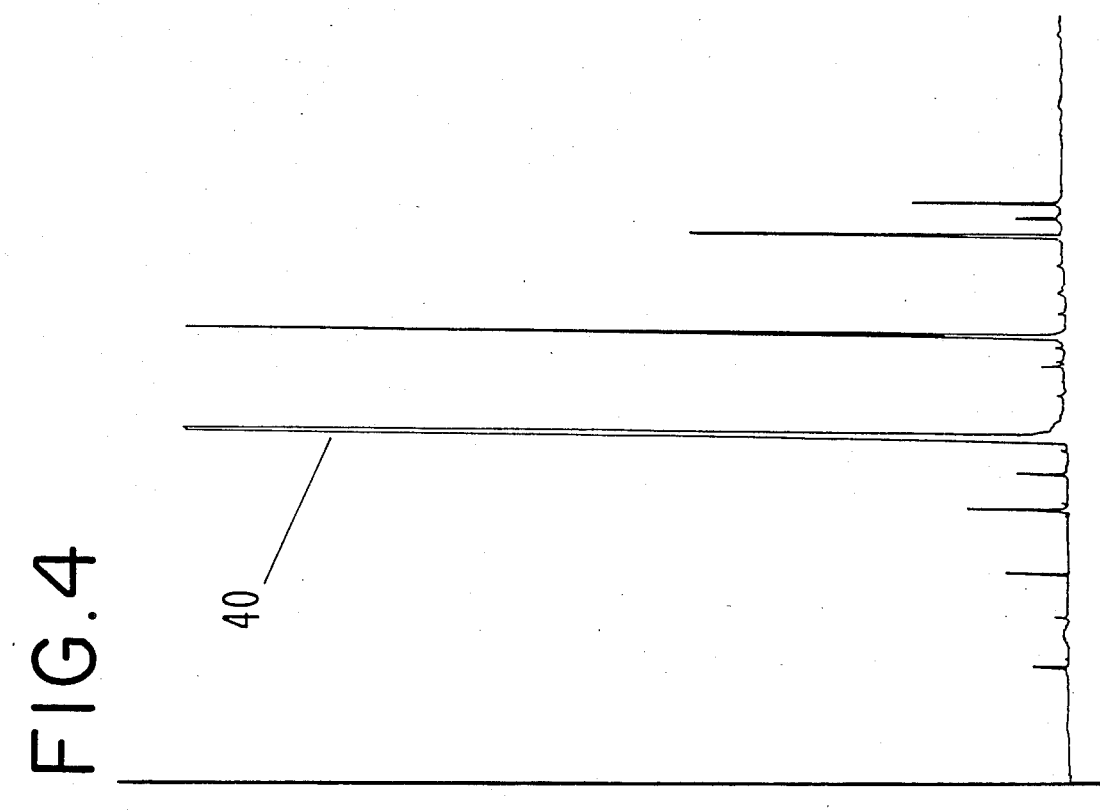

FIG. 4 is the GLC profile for the reaction product of Example II containing the compound having the structure:

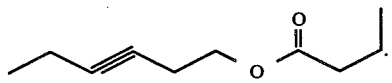

Figure 5:
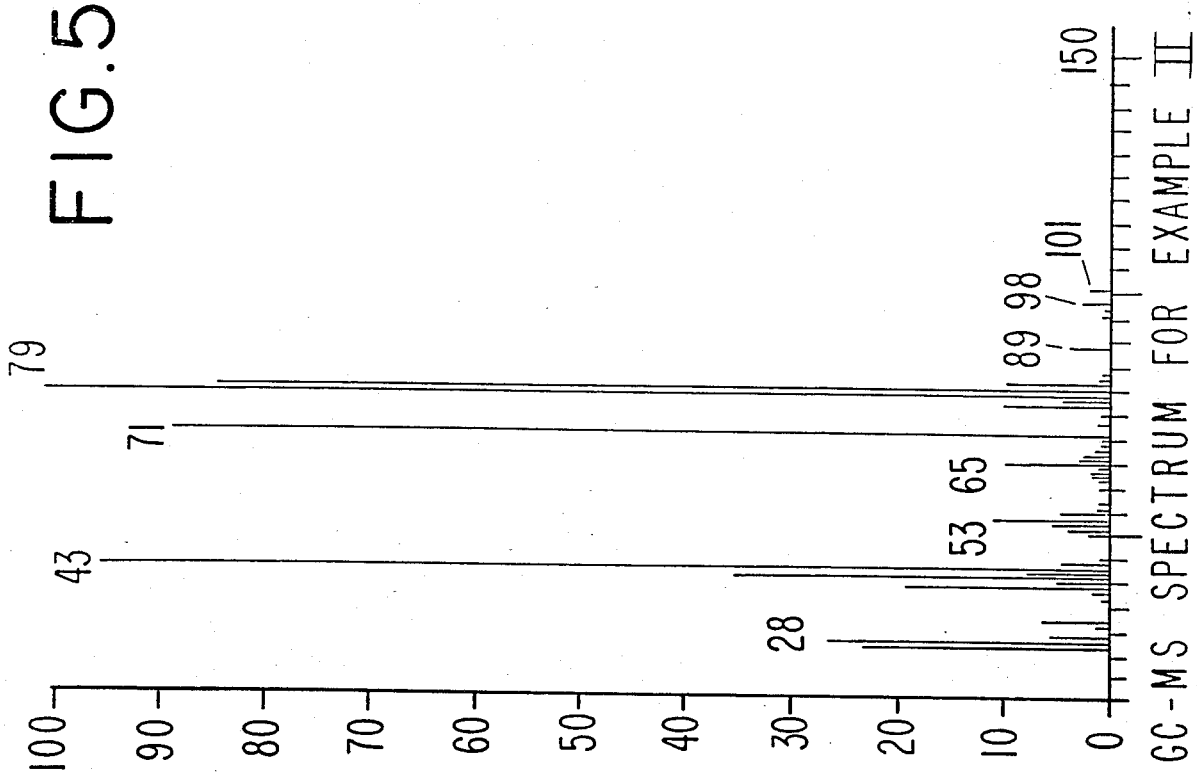

FIG. 5 is the GC-MS spectrum for the compound having the structure:

prepared according to Example II.

FIG. 6 is the NMR spectrum for Fraction 1 of the distillation of the reaction product of Example II containing the compound having the structure:

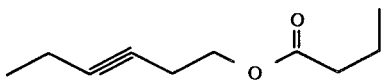

(Conditions: Field strength: 100 MHz; Solvent: CFCl₃).

Figure 7:
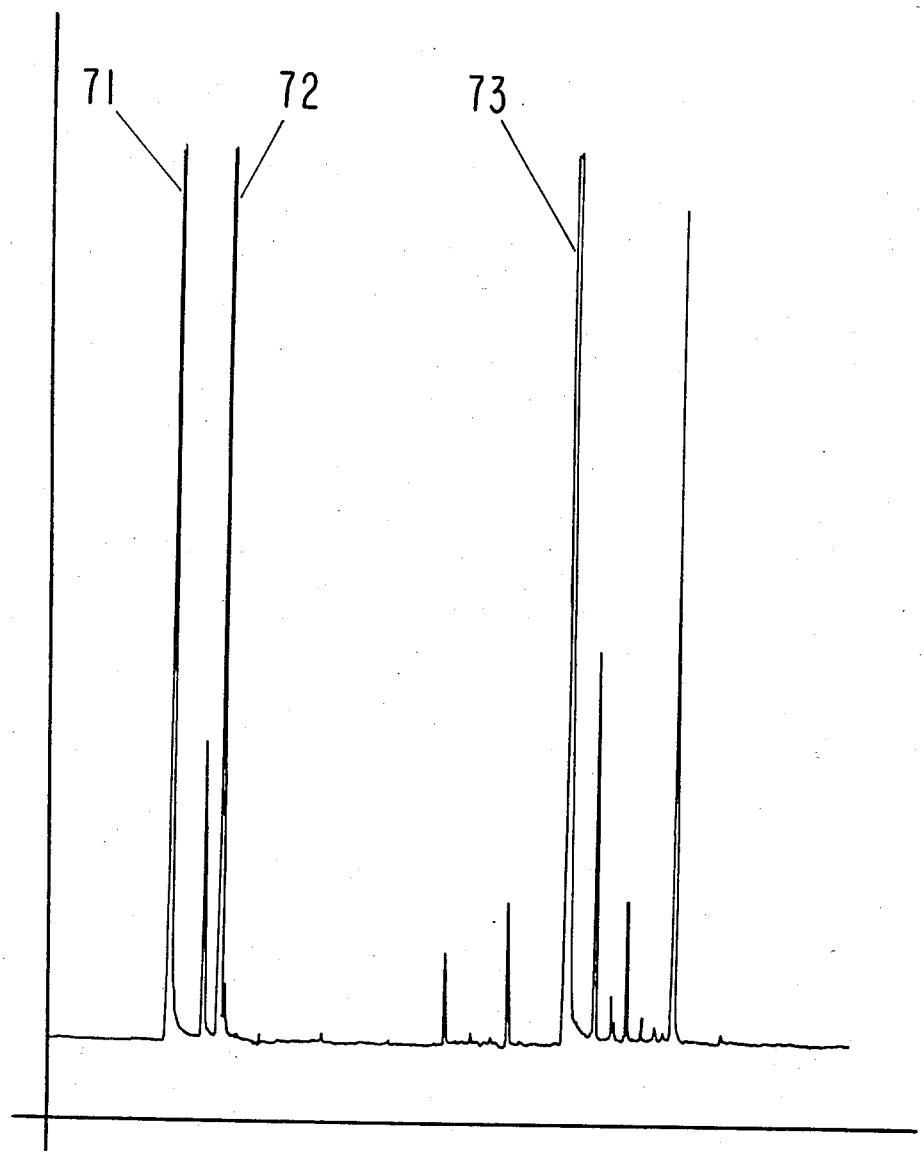

FIG. 7 is the GLC profile for the crude reaction product of Example III containing the compound having the structure:

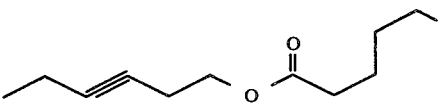

Figure 8:
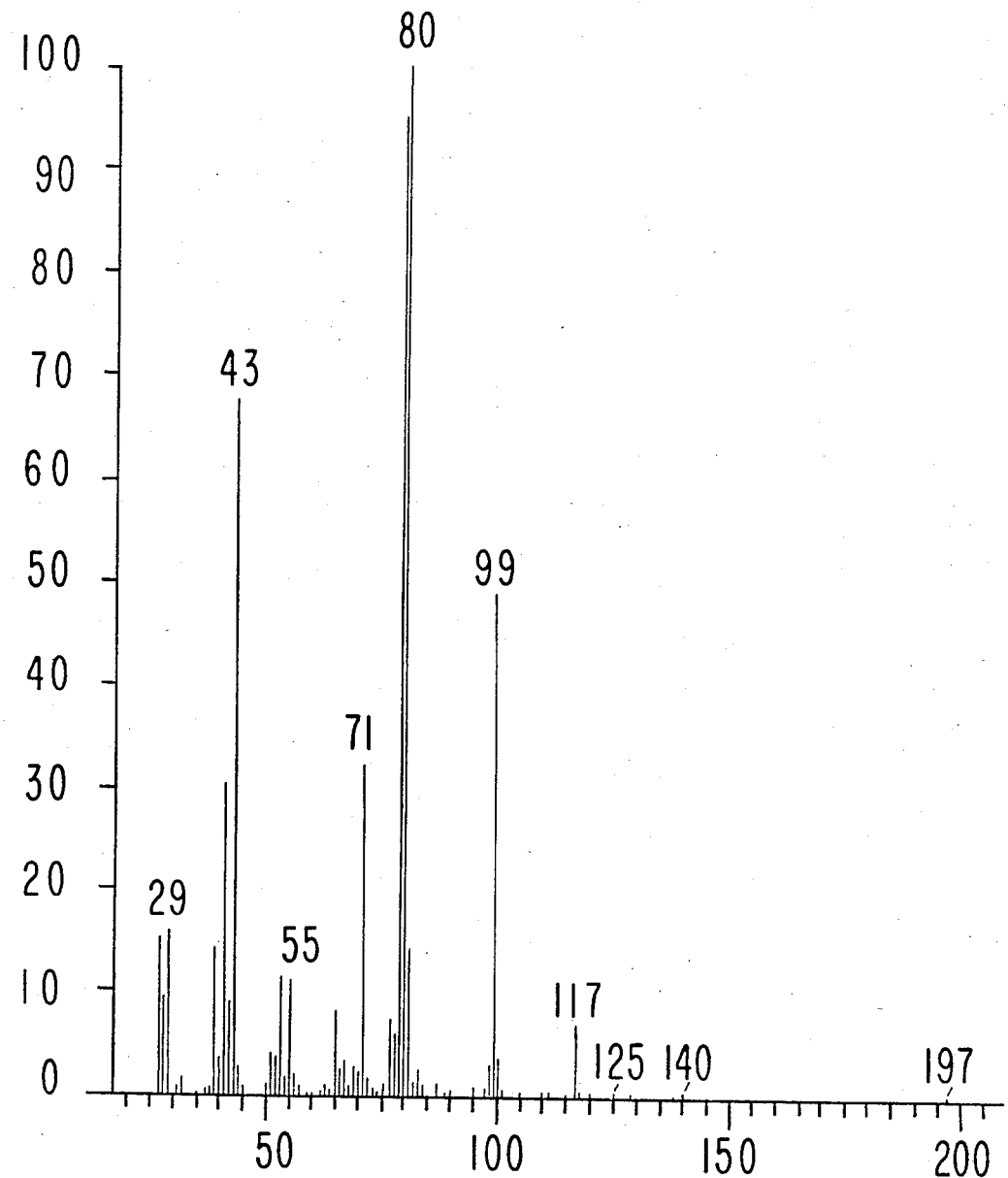

FIG. 8 is the GC-MS spectrum for the compound having the structure:

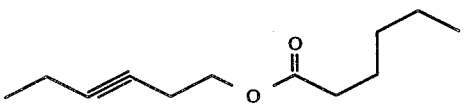

prepared according to Example III.

Figure 9:
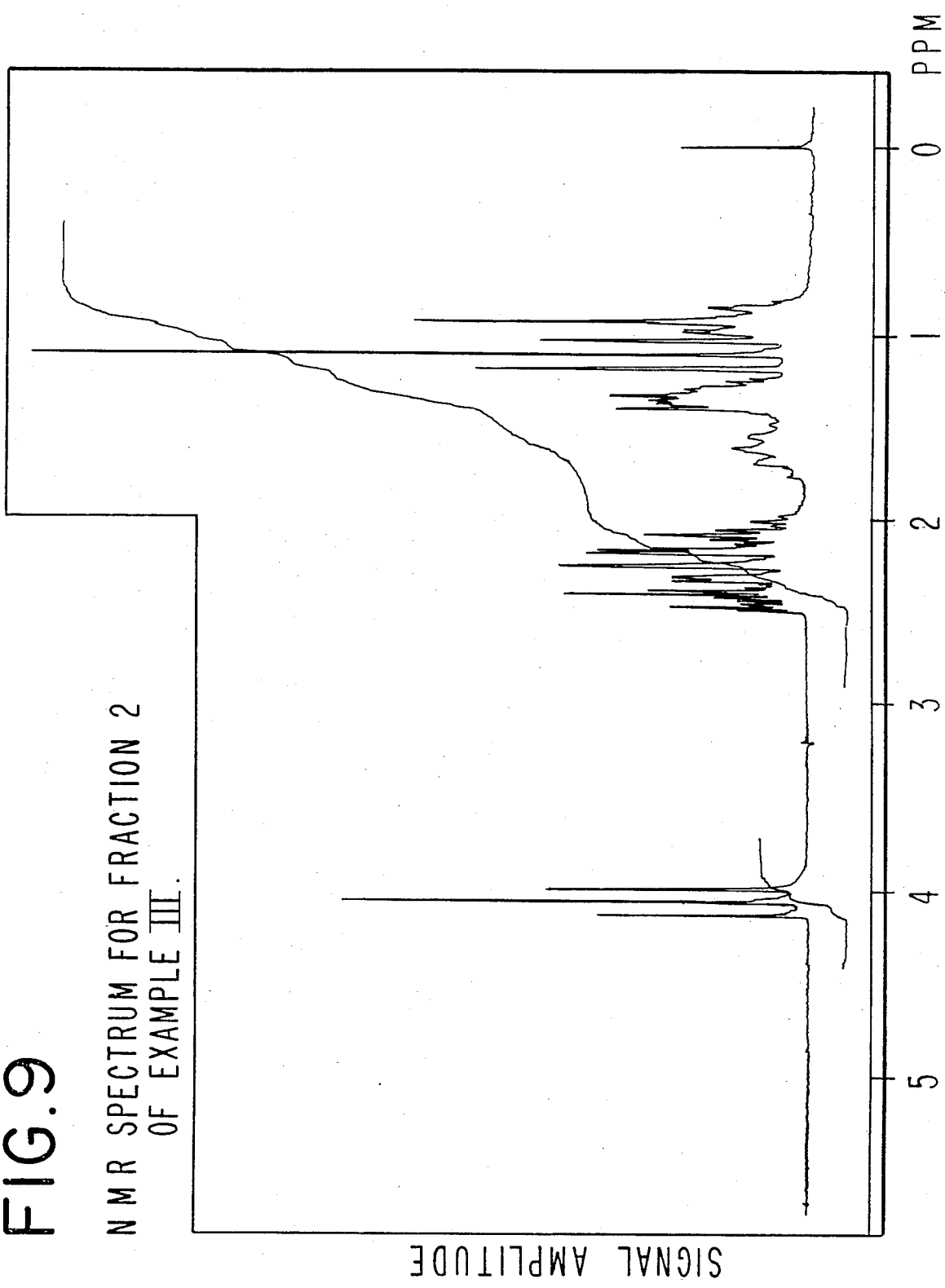

FIG. 9 is the NMR spectrum for Fraction 2 of the distillation of the reaction product of Example III containing the compound having the structure:

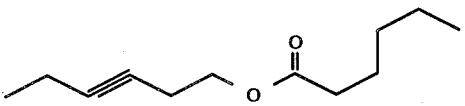

(Conditions: Field strength: 100 MHz; Solvent: CFCl₃).

FIG. 10 is a cut-a-way side elevation view of apparatus used in preparing perfume-containing polymers of our invention.

FIG. 11 is a cross-sectional view taken along lines 11—11 of FIG. 10.

DETAILED DESCRIPTION OF THE DRAWINGS

FIG. 4 is the GLC profile for the reaction product of Example II. (Conditions: 50 m×0.32 mm methyl silicone-fused silica column programmed at 100°–225° C. at 4° C. per minute). The peak indicated by reference numeral 40 is the peak for the compound having the structure:

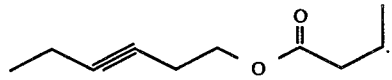

FIG. 7 is the GLC profile for the crude reaction product of Example III. (Conditions: 50 m×0.32 mm methyl silicone-fused silica column programmed at 100°–225° C. at 4° C. per minute). The peak indicated by reference numeral 71 is the peak for the toluene reaction solvent. The peak indicated by reference numeral 22 is the peak for caproic acid. The peak indicated by reference numeral 73 is the peak for 3-hexynyl hexanoate having the structure:

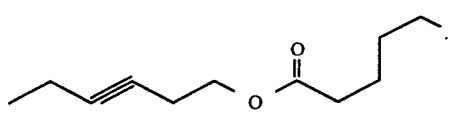

Referring to FIGS. 10 and 11, a thermoplastic polymer, e.g., polyethylene is heated to about 220°–250° F. in a container 212 of the kind illustrated in FIGS. 10 and 11. A fragrance formulation, containing at least one of the compounds defined according to the generic structure:

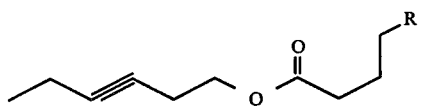

wherein R represents hydrogen or ethyl (hereinafter referred to as "hexynyl alkanoates") is then quickly added to the liquified thermoplastic polymer, the lid 228 is put in place and the agitating means 273 are actuated. The temperature is maintained at about 225° F. and the mixing is continued for about 5–15 minutes. The valve "V" is then opened to allow flow of the molten thermoplastic polymer enriched with fragrance containing at least one of the hexynyl alkanoates of our invention to exit through the orifices 234. The liquid 236 falling through the orifices 234 solidifies almost instantaneously upon impact with the moving cooled conveyor 238 which is operated using rollers 240 and 242. The container 512 is heated using heating coils 212A the heat being supplied by an electric current through power sources 214/216/224 and 222/220/226. Heat may also be supplied via auxiliary steam duct 218. The conveyor 238 bearing cooled pellets 244 moves the cooled pellets into container 245. The lid 228 is fastened to the mixing vessel 212 using bolts 265. The pellets 244 are cooled by means of water cooling bath 248/250/254/256.

THE INVENTION

The invention relates to hexynyl alkanoates defined according to the generic structure:

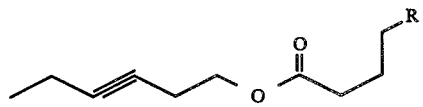

wherein R represents hydrogen or ethyl, for augmenting or enhancing the flavor and/or aroma of consumable materials including foodstuffs, chewing gums, medicinal products, toothpastes, perfumes, colognes and perfumed articles.

Briefly, our invention contemplates augmenting or enhancing the flavors and/or fragrances of such consumable materials as perfumes, perfumed articles (e.g., solid or liquid anionic, cationic, nonionic or zwitterionic detergents, cosmetic powders, hair preparations such as shampoos and perfumed thermoplastic and thermoset resins), colognes, foodstuffs, chewing gums, toothpastes, medicinal products and chewing tobaccos by adding thereto a small but effective amount of at least one of the hexynyl alkanoates defined according to the structure:

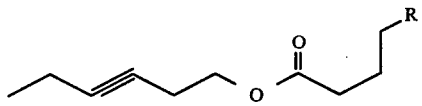

wherein R represents hydrogen or ethyl.

The hexynyl alkanoates of our invention augment, impart or enhance to fragrances sweaty, animalic, leathery, floral, anisic, green, petitgrain, neroli and magnolia aromas with fruity, green herbaceous, floral, chamomile, orange flower, neroli and fresh fruity topnotes.

The hexynyl alkanoates of our invention also impart, augment and/or enhance green, marquisa, passion fruit-like, sweet, fruity, brown sugar-like and maltol-like aromas and green, marquisa, passion fruit-like, sweet, fruity, brown sugar-like, maltol-like, maple and creamy tastes in foodstuffs, chewing gums, medicinal products, chewing gums and chewing tobaccos.

The hexynyl alkanoates of our invention defined according to the structure:

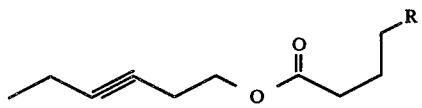

wherein R represents hydrogen or ethyl are produced by esterification of 3-hexyn-1-ol defined according to the structure:

with an alkanoic acid defined according to the structure:

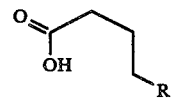

according to the reaction:

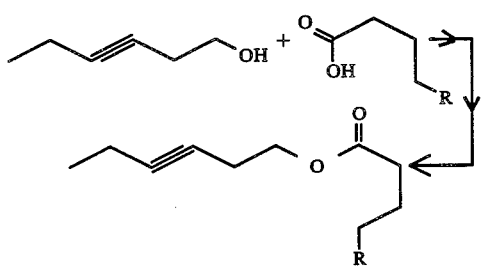

The reaction is carried out in an inert solvent such as toluene using a protonic acid catalyst such as concentrated sulfuric acid. The mole ratio of alkanoic acid to hexynol is preferably about 1:1. The reaction is carried out under reflux conditions for a period of time of between about two and about ten hours. At the end of the reaction, the reaction product is separated from the reaction mass by means well known to those skilled in the art including extraction and fractional distillation.

When the hexynyl alkanoates of our invention are used as food flavor adjuvants, the nature of the co-ingredients included with said hexynyl alkanoates in formulating the product composition will also serve to alter, modify, augment or enhance the organoleptic properties of the ultimate foodstuff treated therewith.

As used herein with regard to flavors, the terms "alter", "modify" and "augment" in their various forms mean "supplying or imparting flavor character or note to otherwise bland, relatively tasteless substances or augmenting the existing flavor characteristics where a natural flavor is deficient in some regard or supplementing the existing flavor impression to modify its quality character or taste".

The term "enhance" is used herein to mean the intensification of a flavor or aroma characteristic or note without the modification of the quality thereof. Thus, "enhancement" of a flavor or aroma means that the enhancement agent does not add any additional flavor nuance.

As used herein the term "foodstuff" includes both solid and liquid ingestible materials which usually do but need not have nutritional value. Thus, foodstuffs include soups, convenience foods, beverages, dairy products, candies, vegetables, cereals, soft drinks, snacks and the like.

As used herein the term "medicinal product" includes both solids and liquids which are ingestible, non-toxic materials which have medicinal value such as cough syrup, cough drops, aspirin and chewable medicinal tablets.

The term "chewing gum" is intended to mean a composition which comprises a substantially water insoluble chewable plastic gum base such as chicle or substitutes therefor including jelutong guttakay rubber or certain comestible natural or synthetic resins or waxes. Incorporated with the gum base in admixture therewith may be plasticizers or softening agents e.g. gelatin and a flavoring composition which incorporates one or both of the hexynyl alkanoates of our invention, and, in addition, sweetening agents which may be sugars including sucrose or dextrose and/or artificial sweeteners such as cyclamates or saccharine. Other optional ingredients may also be present.

Substances suitable for use herein as co-ingredients or flavoring adjuvants are well known in the art for such use being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have any unacceptable aroma or taste nuances. Such materials may be in general be characterized as flavoring adjuvants or vehicles comprising broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy-anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar, carrageenan: cellulose and cellulose derivatives such as carboxymethylcellulose and methyl cellulose; natural and synthetic gums such as gum arabic, gum tragacanth: gelatin, proteinaceous materials, lipids, carbohydrates: starches, pectins and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, butters and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethylacrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehye, betadamascenone, alphadamascone, beta-damascone, acetophenone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone,2-pentenal and propanal; alcohols such as 1-butanol, benzyl alcohol, 1-borneol, trans-2-buten-1-ol, ethanol, geraniol, 1-hexanol, 2-heptanol, trans-2-hexen-1-ol, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpin hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha methylbutyrate, ethyl propionate, ethyl salicylate, trans-2-hexenyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alpha-phellandrene, beta-phellandrene, p-cymene, 1-alpha pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methylethylpyrazine, tetramethylpyrazine, trimethylpyrazine; essential oils such as jasmine absolute, cassia oil, cinnamon bark oil, black pepper oleoresin oil, oil of black pepper, rose absolute, orris absolute, oil of cubeb, oil of coriander, oil of pimento leaf, oil of patchouli, oil of nutmeg, lemon essential oil, safran oil. Bulgarian rose, capsicum, yara yara and vanilla; other lactones such as gamma-nonalactone, gamma-decalactone, gamma-dodecalactone, gamma-undecalactone, delta-decalactone, delta-dodecalactone, delta-undecalactone; sulfides, e.g., methyl sulfide and other materials such as maltol, ethyl maltol and acetals (e.g. 1,1-diethoxyethane, 1,1-dimethoxyethane and dimethoxymethane), piperazine, chavicine and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the hexynyl alkanoates of our invention by not covering or spoiling the organoleptic properties (aroma and/or taste) thereof; (ii) be non-reactive with the hexynyl alkanoates of our invention; and (iii) be capable of providing an environment in which the hexynyl alkanoates of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of hexynyl alkanoates of our invention employed in a particular instance can vary over a relatively wide range, depending upon the desired organoleptic effects to be achieved. Thus, correspondingly greater amounts would be necessary in those instances wherein the ultimate food composition to be flavored (e.g., with a passion fruit flavor) is relatively bland to the taste, whereas relatively minor quantities may suffice for purpose of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, beverage (e.g. with a passion fruit flavor), toothpaste per se or flavoring composition.

The use of insufficient quantities of hexynyl alkanoates will, of course, substantially vitiate any possibility of obtaining the desired results while excess quantities prove needlessly costly and, in extreme cases, may disrupt the flavor-aroma balance thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions, alcoholic beverage compositions and toothpaste compositions, it is found that quantities of hexynyl alkanoates ranging from a small but effective amount, e.g., 0.5 parts per million up to about 100 parts per million based on total composition, are suitable. Concentrations in excess of the maximum quantity stated are not normally recommended since they fail to provide commensurate enchancement or organoleptic properties. In those instances wherein the hexynyl alkanoates are added to the foodstuff as an integral component of a flavoring composition, it is, of course, essential that the total quantity of flavoring composition employed be sufficient to yield an effective hexynyl alkanoate concentration in the foodstuff product.

Food flavoring compositions prepared in accordance with the present invention preferably contain the hexynyl alkanoates in concentrations ranging from about 0.1% up to about 25% by weight based on the total weight of the said flavoring composition.

The compositions described herein can be prepared according to conventional techniques well known as typified by cake batters, alcoholic beverages (e.g., with a passion fruit flavor) and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the hexynyl alkanoates with, for example, gum arabic, gum tragacanth, xanthan gum, guar gum, carrageenan and the like, and thereafter spray-drying the resultant mixture whereby to obtain the particulate solid product. Pre-prepared flavor mixes in powder form, e.g., with a passion fruit flavor mix are obtained by mixing the dried solid components, e.g., starch, sugar and the like, and the hexynyl alkanoates in a dry blender until the reguisite degree of uniformity is achieved.

It is presently preferred to combine with the hexynyl alkanoates of our invention the following adjuvants:

oil of nutmeg;
clove oil;
almond oil;
almond paste;
$\gamma$-nonalactone;
$\gamma$-undecalactone;
$\gamma$-decalactone;
$\gamma$-dodecalactone;
$\delta$-dodecalactone;
$\delta$-undecalactone;
$\delta$-decalactone;
$\delta$-nonalactone;
$\delta$-octalactone;
$\beta$-damascenone;
$\alpha$-damascone;
$\beta$-damascone;
acetaldehyde;
acetaldehyde diethylacetal;
acetoxyethoxyethane;
cinnamic alcohol;
cinammic aldehyde;
cinnamic aldehyde diethylacetal;
diethylacetal of 3-phenyl-4-pentenal;
diethylacetal of 2-phenyl-5-hexenal;

n-methylanthranilate;
maltol;
ethylmaltol;
propylmaltol;
2,5-dimethyl-3-hydroxy-4,5-dihydrofuran-4-one; and
2,5-diethyl-3-hydroxy-4,5-dihydrofuran-4-one.

The hexynyl alkanoates of our invention can be used to contribute sweaty, animalic, leathery, floral, anisic, green, petitgrain, neroli and magnolia aromas with fruity, green, herbaceous, floral, chamomile, orange flower, neroli and fresh fruity topnotes to perfumed articles, perfume compositions and colognes. As olfactory agents, the hexynyl alkanoates of our invention can be formulated into or used as components of a "perfume composition".

The term "perfume composition" is used herein to mean a mixture of organic compounds including, for example, alcohols, aldehydes, ketones, nitriles, ethers, lactones, esters other than the hexynyl alkanoates of our invention, hydrocarbons, natural essential oils and synthetic essential oils which are admixed so that the combined odors of the individual components produce a pleasant or desired fragrance. Such perfume compositions usually contain: (a) tha main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the individual hexynyl alkanoates of this invention or mixtures thereof, can be used to alter the aroma characteristics of a perfume composition by, for example, highlighting or moderating the olfactory reaction contributed by another ingredient in the composition.

The amount of hexynyl alkanoates of our invention which will be effective in perfume compositions depends on many factors including the other ingredients, their amounts and the effects which are desired. It has been found that perfume compositions containing as little as 2% of the hexynyl alkanoates of our invention of even less, can be used to impart, augment or enhance sweaty, animalic, leathery, floral, anisic, green, petitgrain, neroli and magnolia aromas with fruity, green, herbaceous, floral, chamomile, orange flower, neroli and fresh fruity topnotes to soaps, cosmetics, and other products including solid or liquid anionic, cationic, nonionic or zwitterionic detergents and perfumed plastics. The amount employed can range up to 50% or higher and will depend on considerations of cost, nature of the end product and the effects desired on the finished product and the particular fragrance sought.

The hexynyl alkanoates of our invention can be used alone or in a perfume composition as an olfactory component in detergents and soaps, space odorants and deodorants; perfumes, colognes, toilet water, bath salts; hair preparations such as lacquers, brilliantines, pomades and shampoos; cosmetic preparations such as creams, deodorants, hand lotions and sun screens; powders such as talcs, dusting powders, face powders and the like. When used as an olfactory component for perfumed articles, as little as 0.01% of the hexynyl alkanoates of our invention will suffice to impart, augment or enhance interesting, sweaty, animalic, leathery, floral, anisic, green, petitgrain, neroli and magnolia aromas with fruity, green, herbaceous, floral, chamomile, orange flower, neroli and fresh fruity topnotes. Generally, no more than 2.5% based on the weight of the perfumed article is required. Accordingly, the range of hexynyl alkanoates in perfumed articles varies from about 0.01% up to 2.5% by weight of said perfumed article.

In addition, the perfume composition can contain a vehicle or carrier for the hexynyl alkanoates of our invention taken alone or taken further together with other ingredients. The vehicle can be a liquid such as an alcohol such as ethanol; a glycol such as propylene glycol or the like. The carrier can be an adsorbent solid such as a gum (e.g., guar gum, xanthan gum and the like) or components for encapsulating the composition such as gelatin (as by coacervation) or a urea formaldehyde prepolymer (for forming a polymerized capsule wall around a central perfume oil center located within the capsule).

The following examples are given to illustrate embodiments of this invention as it is presently preferred to practice it. It will be understood that these examples are illustrative and that the invention is not to be considered as restricted thereto except as indicated in the appended claims.

EXAMPLE I

Preparation of 3-Hexynyl Acetate

Reaction:

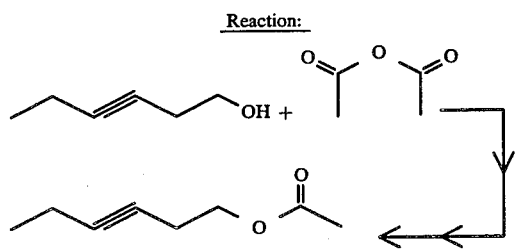

Into a 250 ml reaction flask equipped with condenser, heating mantle, magnetic stirrer and thermometer is placed 30.6 grams of acetic anhydride (0.3 moles) and 29.4 grams of 3-hexyn-1-ol (0.3 moles). The reaction mass is heated to reflux for a period of four hours. At the end of the four hour period, the crude reaction product is transferred to a separatory funnel and washed with two volumes of 10% sodium carbonate followed by two volumes of saturated sodium chloride solution. The resulting crude material is then distilled on a short path column.

Figure 1:
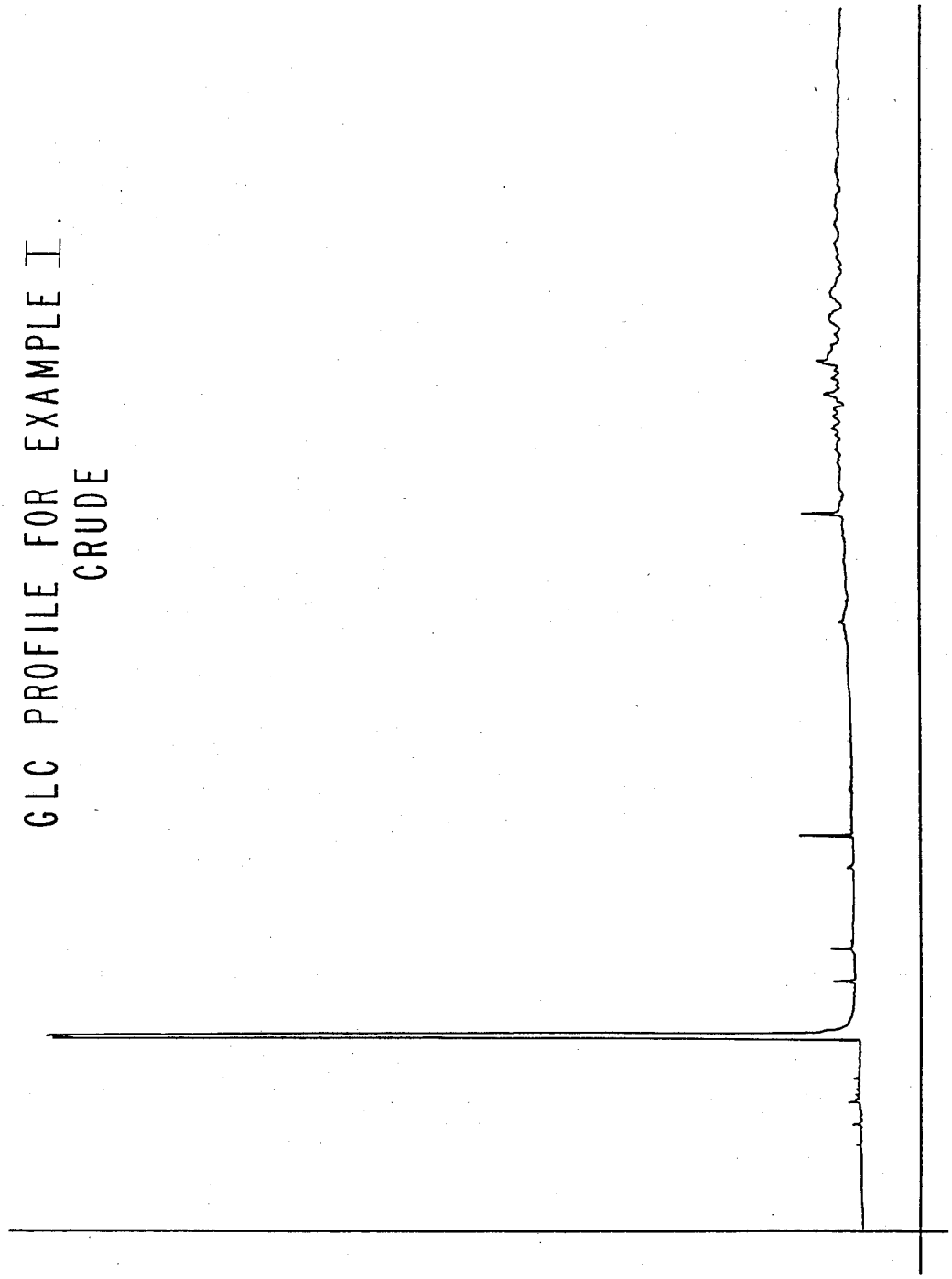
FIG. 1 is a GLC profile for the crude reaction product of Example I containing the compound having the structure.

FIG. 1 is the GLC profile for the crude reaction product containing the compound having the structure:

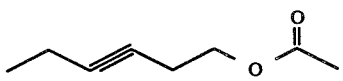

(Conditions: 50 m × 0.32 mm methyl silicone-fused silica column programmed at 100°–225° C. at 4° C. per minute).

FIG. 2 is the GC-MS spectrum for the compound having the structure:

FIG. 3 is the NMR spectrum for the compound having the structure:

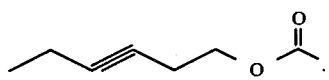

(Conditions: Field strength: 100 MHz; Solvent: CFCl$_3$).

The resulting product has a fruity, green aroma profile with a balsamic and cinnamon topnote as well as a cucumber undertone.

EXAMPLE II

Preparation of 3-Hexynyl Butyrate

Reaction:

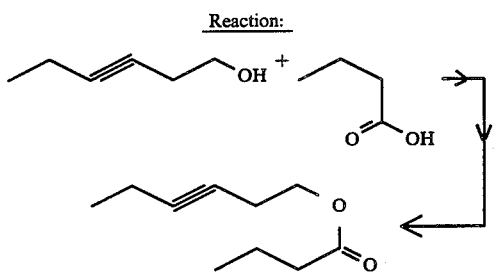

Into a 250 ml reaction flask equipped with condenser, magnetic stirrer, heating mantle and Dean Stark trap is placed 26.4 grams (0.3 moles) of butyric acid; 29.4 grams (0.3 moles) of 3-hexyn-1-ol; 100 ml toluene and 0.2 ml of concentrated sulfuric acid.

The reaction mass is heated to reflux and refluxed for a period of four hours.

At the end of the four hour period, the reaction mass is cooled and the crude product is transferred to a separatory funnel and washed with two volumes of 10% sodium carbonate followed by two volumes of saturated sodium chloride. The resulting crude reaction product is then distilled on a short path column at a vapor temperature of 80° C. at 1.0 mm/Hg. pressure.

FIG. 4 is the GLC profile for the crude reaction product (Conditions: 50 m×0.32 mm methyl silicone-fused silica column programmed at 100°–225° C. at 4° C. per minute). The peak indicated by reference numeral 40 is the peak for the compound having the structure:

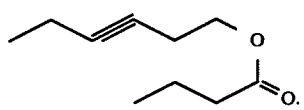

FIG. 5 is the GC-MS spectrum for the compound having the structure:

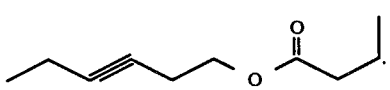

FIG. 6 is the NMR spectrum for the distillation product having the structure:

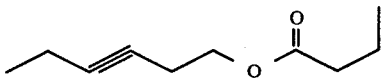

(Conditions: Field strength: 100 MHz; Solvent: CFCl$_3$).

The resulting compound from a fragrance standpoint has a sweaty, animalic and leathery aroma with fruity, green, herbaceous floral, chamomile, orange flower and neroli topnotes. From a flavor point of view, the resulting compound has a green, marquisa and passion fruit aroma and taste profile.

EXAMPLE III

Preparation of 3-Hexynyl Hexanoate

Reaction:

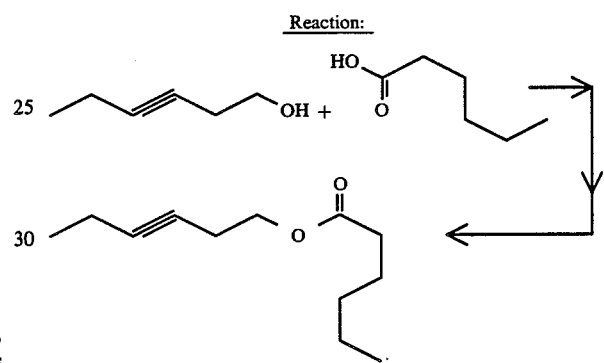

Into a 250 ml reaction flask equipped with condenser, stirrer, heating mantle, thermometer and Dean Stark trap is placed 29.4 grams (0.3 moles) of 3-hexyn-1-ol; 34.8 grams (0.3 moles) of n-hexanoic acid; 100 ml toluene and 0.2 ml concentrated sulfuric acid. With stirring, the reaction mass is refluxed for a period of four hours. At the end of the four hour period, the reaction mass is then cooled to room temperature and washed with two volumes of 10% sodium carbonate followed by two volumes of saturated sodium chloride solution. The reaction mass is then distilled on a one plate short path column yielding the following fractions:

| Fraction No. | Vapor Temp. (°C.) | Liquid Temp. (°C.) | Vacuum mm/Hg. Pressure |
|---|---|---|---|
| 1 | 67 | 70 | 0.25 |
| 2 | 68 | 71 | 0.25 |
| 3 | 50 | 110 | 4.00 |

FIG. 7 is the GLC profile for the crude reaction product prior to distillation (Conditions: 50 m×0.32 mm methyl silicone-fused silica column programmed at 100°–225° C. at 4° C. per minute). The peak indicated by reference numeral 71 is the peak for the toluene solvent. The peak indicated by reference numeral 72 is the peak for the caproic acid reactant and the peak indicated by reference numeral 73 is the peak for the 3-hexynyl hexonate having the structure:

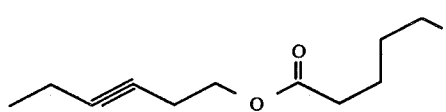

FIG. 8 is the GC-MS profile for the 3-hexynyl hexonate having the structure:

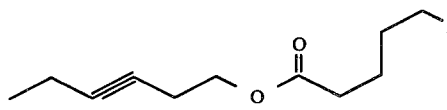

FIG. 9 is the NMR spectrum for Fraction 2 of the foregoing distillation consisting of 3-hexynyl hexonate having the structure:

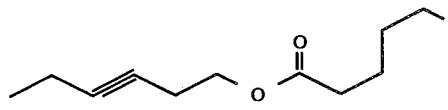

From a fragrance standpoint the 3-hexynyl hexonate has a floral, anisic, green, petitgrain, neroli and magnolia aroma with fresh fruity topnotes.

From a food flavor standpoint the 3-hexynyl hexonate having the structure:

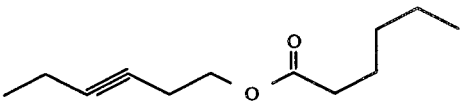

has a fruity, marquisa, brown sugar-like and maltol-like aroma with a fruity, marquisa-like, brown sugar-like, maltol-like, maple and creamy taste profile at 1 ppm.

EXAMPLE IV

Herbal Fragrances

The following mixtures are prepared:

| Ingredients | Parts by Weight IV(A) | IV(B) |
|---|---|---|
| Amyl cinnamic aldehyde | 20 | 20 |
| Phenyl acetaldehyde dimethyl acetal | 4 | 4 |
| Thyme oil white | 8 | 8 |
| Sauge sclaree French | 8 | 8 |
| Galbanum oil | 4 | 4 |
| Geranyl acetate | 10 | 10 |
| Juniper berry oil | 4 | 4 |
| Methyl octynyl carbonate | 2 | 2 |
| Linalyl acetate | 10 | 10 |
| Dihydro methyl jasmonate | 20 | 20 |
| The compound having the structure: 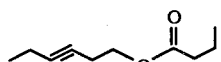 prepared according to Example II. | 0 | 12 |
| The compound having the structure: 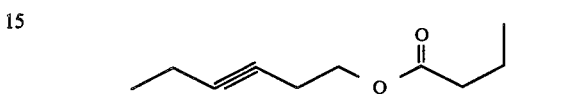 prepared according to Example III. | 12 | 0 |

The compound having the structure:

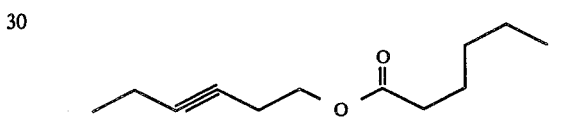

prepared according to Example II imparts a sweaty, animalic, leathery undertone with fruity, green, herbaceous, floral, chamomile, orange flower and neroli topnotes to this herbal fragrance. Accordingly, the herbal fragrance can be described as "herbal with sweaty, animalic and leathery undertones and fruity, green, herbaceous, floral, chamomile, orange flower and neroli topnotes".

The compound having the structure:

prepared according to Example III used in Example IV(B) imparts to the herbal fragrance a floral, anisic, green, petitgrain, neroli and magnolia undertone with fresh fruity topnotes. Accordingly, the perfume composition of Example IV(B) can be described as "an herbal fragrance with floral, anisic, green, petitgrain, neroli and magnolia undertones and fresh, fruity topnotes".

EXAMPLE V

Preparation of a Cosmetic Powder Composition

A cosmetic powder is prepared by mixing in a ball mill 100 grams of talcum powder with 0.25 grams of the perfume substance set forth in Table I below. The resulting cosmetic powders have excellent aroma profiles as indicated in Table I below:

TABLE I

| Perfume Substance | Aroma Profile |
|---|---|
| The compound having the structure: prepared according to Example II. | A sweaty, animalic and leathery aroma with fruity, green, herbaceous, floral, chamomile, orange flower and neroli topnotes. |
| The compound having the structure: prepared according to Example III. | A floral, anisic, green, petitgrain, neroli, magnolia aroma with fresh, fruity topnotes. |
| Perfume composition of Example IV(A). | A herbal fragrance with sweaty, animalic and leathery undertones and |

TABLE I-continued

| Perfume Substance | Aroma Profile |
|---|---|
| | fruity, green, herbaceous, floral, chamomile, orange flower and neroli topnotes. |
| Perfume composiiton of Example IV(B). | A herbal fragrance with floral, anisic, green, petitgrain, neroli and magnolia undertones and fresh, fruity topnotes. |

EXAMPLE VI

Preparation of Soap Composition 100 grams of soap chips are mixed with 1 gram of each of the perfume materials of Table I of Example V until a substantially homogeneous composition is obtained. The resulting mixture is melted and maintained at 10 atmospheres pressure at a temperature of 180° C. for a period of 4 hours. At the end of the 4 hour period, the resulting homogeneous mixture is cooled. The perfumed soap composition manifests an excellent aroma character as set forth in Table I of Example V.

EXAMPLE VII

Preparation of a Detergent Composition

A granular detergent composition is prepared according to Example IX of Canadian Pat. No. 1,004,566 (the disclosure of which is incorporated by reference herein) containing the following ingredients:

| Component | Weight % |
|---|---|
| Anhydrous sodium carbonate | 30.0 |
| Hydrated sodium silicate (81.5% solids, SiO$_2$:Na$_2$O ratio-2.1:1 by weight) | 20.0 |
| Coconut alcohol condensed with 6 molar proportions of ethylene oxide | 10.0 |
| Sodium citrate dihydrate | 10.0 |
| Sodium dichlorocyanuarte dihydrate | 3.8 |
| Polyethylene glycol (available under the trademark CARBOWAX ® 4000 M.W. 3000-3700 | 2.0 |
| Dimethyl silicone | 0.8 |
| Anhydrous sodium sulfate | 15.5 |
| Perfume substance as set forth in Table I of Example V | 5.9 |

The resulting detergent compositions have excellent aromas as set forth in Table I of Example V.

EXAMPLE VIII

Preparation of a Detergent Composition

A detergent is prepared from the following ingredients according to Example I of Canadian Pat. No. 1,007,948 (the disclosure of which is incorporated herein by reference):

| Ingredient | Parts by Weight |
|---|---|
| Neodol 45-11 (a C$_{14}$-C$_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of this detergent is admixed individually with 0.15 grams of each of the perfumery substances of Table I of Example V. Each of the detergents has excellent aromas as set forth in Table I of Example V.

EXAMPLE IX

Perfumed Liquid Detergent

Concentrated liquid detergents with aroma nuances as set forth in Table I of Example V containing 0.10%, 0.15% and 0.20% of each of the perfumery substances of Table I of Example V are prepared. They are prepared by adding and homogeneously admixing the appropriate quantity of each of the perfumery substances of Table I of Example V in the liquid detergent. The detergents all possess excellent aromas as set forth in Table I of Example V.

EXAMPLE X

Cologne and Handkerchief Perfumes

The perfume substances of Table I of Example V are each incorporated separately into colognes at concentrations of 1.5%, 2.0%, 2.5%, 3.0%, 4.0% and 5.0% in 70%, 75%, 80%, 85% and 90% aqueous ethanol solutions; and into handkerchief perfumes at concentrations of 15%, 20%, 30% and 40% (in 80%, 85%, 90% and 95% aqueous ethanol solutions). Distinct and definitive strong fragrances are imparted to the colognes and to the handkerchief perfumes at the levels indicated according to the aroma profiles as set forth in Table I of Example V.

EXAMPLE XI

Perfumed Plastics

Scented polyethylene pellets having pronounced aromas as set forth in Table I of Example V are prepared as follows:

Seventy-five pounds of polyethylene having a melting point of about 220° F. is heated to about 230° F. in a container of the kind illustrated in FIGS. 10 and 11. Twenty-five pounds of the fragrance materials of Table I of Example V is then quickly added to the liquified polyethylene, the lid 228 is put in place and the agitating means 273 are actuated. The temperature is maintained at about 225° F. and the mixing is continued for about 5-15 minutes. The valve "V" is then opened to allow flow of the molten polyethylene enriched with the aroma containing material to exit through the orifices 234. The liquid falling through the orifices 234 solidifies almost instantaneously upon impact with the moving cooled conveyor 238. Polyethylene beads or pellets 244 having pronounced aromas as set forth in Table I of Example V are thus formed. Analysis demonstrates that the pellets contain about 25% of the aroma substance of Table I of Example V so that almost no loss in the scenting substances occur. These pellets may be called "master pellets".

Fifty pounds of the aroma substance-containing master pellets are then added to one thousand pounds of unscented polyethylene powder and the mass is heated to a liquid state. The liquid is molded into thin sheets of films. The thin sheets of films have pronounced aromas as set forth in Table I of Example V. The sheets of films are cut into strips ¼" in width×3" in length and employed in standard air freshening apparatus.

On operation of the standard air freshening apparatus as a room air freshener, after four minutes, the room has an aesthetically pleasing aroma as set forth in Table I of Example V with no foul odor being present.

EXAMPLE XII

One hundred pounds of polypropylene are heated to about 300° F. Thirty pounds of the essences or the perfume substances as described in Table I of Example V, supra, are added to the liquified polypropylene. The procedure is carried out in the apparatus shown in FIGS. 10 and 11. After mixing for about eight minutes, the valve "V" is opened to allow the exit of polypropylene scented material mixture whereby solid pellets having a pronounced perfume aroma as set forth in in Table I of Example V are formed on the conveyor 238. The pellets 244 thus formed are then admixed with about twenty times their weight of unscented polypropylene and the mixture is heated and molded into "spaghetti" tows. The spaghetti tows are cut into small cylinders approximately 0.1 inches in length×0.02 inches in diameter. The cylinders have a strong and pleasant aroma as set forth in Table I of Example V, supra.

The cylinders are used in standard air freshening apparatus to produce aesthetically pleasing faint scents with no foul odor in environments surrounding the air freshening apparatus, the scents described in Table I of Example V, supra.

EXAMPLE XIII

Tropical Fruit/Coconut Flavors

The following basic tropical fruit/coconut flavor is prepared:

| Ingredients | Parts by Weight |
| --- | --- |
| 2,5-dimethyl-3-hydroxy-4,5-dihydrofuran-4-one | 4.0 |
| 2-methyl-5-ethylfuran | 0.3 |
| 2-acetylfuran | 2.0 |
| almond oil | 1.2 |
| vanillin natural | 12.0 |
| γ-nonalactone | 3.0 |
| δ-dodecalactone | 4.8 |
| maltol | 3.2 |

This flavor formulation is divided into 3 portions. Eight parts by weight of the first portion is combined with 2 parts by weight of 3-hexynyl hexanoate produced according to Example III having the structure:

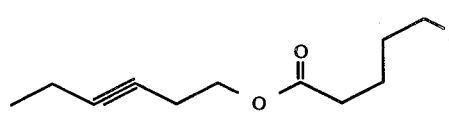

Eight parts by weight of the second portion is combined with 2 parts by weight of 3-hexynyl-2-butyrate having the structure:

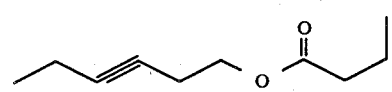

prepared according to Example II.

Nothing is added to the third part.

The three flavors are compared in water at the rate of 5 ppm and evaluated by a bench panel. The two flavors containing the hexynyl alkanoates of our invention having the structures:

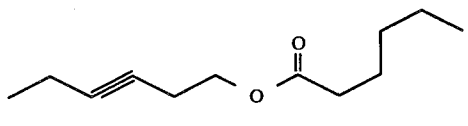

and

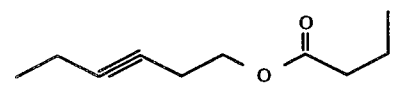

produced in addition to a fuller coconut related note, a "marquisa" flavor nuance simultaneously with a sweet taste. The "marquisa" taste and aroma nuance is reminiscent of "passion fruit" flavor and aroma. The flavors are useful in preparing a "pina colada" beverage as set forth in Example XIV, infra.

Therefore, the flavors containing the hexynyl alkanoates of our invention are considered by the bench panel as being better and more suitable flavors for synthetic tropical fruit flavors having coconut nuances and having unique flavor effects and having the ability to be combined with natural coconut milk in order to retard spoilage.

Spoilage in natural coconut milk is prevented while maintaining the coconut milk at 40° C. for a period of 10 days.

EXAMPLE XIV

A "pina colada" mix is prepared by intimately admixing 4 grams of 3-hexynyl hexanoate having the structure:

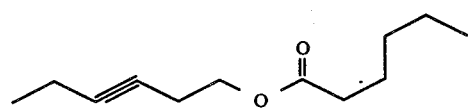

prepared according to Example II, and 4 grams of 3-hexynyl butyrate having the structure:

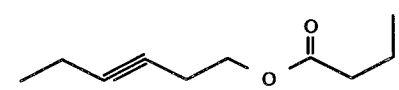

prepared according to Example III together with 10 grams of coconut milk natural.

The resulting mixture is admixed with 50 grams of xanthan gum and the resulting emulsion is spary-dried with a Bowen Lab Model Drier utilizing 260 cfm of air with an inlet temperature of 500° F., an outlet temperature of 200° F. and a wheel speed of 50,000 rpm. The resulting powder is then intimately admixed with a standard "pina colada" alcoholic beverage. The resulting beverage has a much more natural tropical fruit/coconut flavor than the standard "pina colada" alcoholic beverage taken alone.

EXAMPLE XV

A. Powder Flavor Composition

20 Grams of the flavor composition of Example XIII is emulsified in a solution containing 300 grams of gum acacia and 700 grams of water. The emulsion is spray-dried with a Bowen Lab Model Drier utilizing 260 cfm of air with an inlet temperature of 500° F., an outlet temperature of 200° F. and a wheel speed of 50,000 rpm.

B. Sustained Release Flavor

The following mixture is prepared:

| Ingredients | Parts by Weight |
|---|---|
| Liquid coconut flavor containing one of the γ-methyl-γ-cycloalkyl buytrolacetones of Example XIII | 20.0 |
| Propylene glycol | 9.0 |
| CAB-O-SIL ® M-5 (brand of silica produced by the Cabot Corporation, 125 High Street, Boston, Massachusetts 02110 Physical properties: Surface Area: 200 m$^2$/gm Nomianl particle size: 0.012 microns Density: 2.3 lbs/cu. ft. | 5.0 |

The CAB-O-SIL ® is dispersed in the liquid tropical fruit/coconut flavor composition of Example XIII with vigorous stirring thereby resulting in a viscous liquid. 71 Parts by weight of the powder flavor composition of Part A, supra, is then blended into the said viscous liquid with stirring at 25° C. for a period of 30 minutes resulting in a dry, free-flowing, sustained release flavor powder.

EXAMPLE XVI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XIII (containing one of the hexynyl alkanoates prepared according to Example II or Example III) is added to the solution which is then homogenized to form an emulsion having a particle size typically in the range of 5-40 microns. The material is kept at 120° F. under which conditions the gelatin will not gel.

Coacervation is induced by adding, slowly and uniformly, 40 parts by weight of 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate 65° F. The resulting gelled coacervate may be filtered and washed with water at temperatures below the melting point of gelatin to remove the salt.

Hardening of the filtered cake in this example is effected by washing with 200 parts by weight of 30% solution of formaldehyde in water. The cake is then thoroughly washed with water to remove the residual formaldehyde.

EXAMPLE XVII

Chewing Gum

100 Parts by weight of chicle are mixed with 4 parts by weight of the flavor prepared in accordance with Example XV. 300 parts sucrose and 100 parts corn syrup are added. Mixing is effected in a ribbon blender with jacketed side walls of the type manufactured by the Baker Perkins Company.

The resultant chewing gum blend is then manufactured into strips 1 inch in width and 0.1 inch in thickness. The strips 1 inch in width and 0.1 inch in thickness. The strips are cut into lengths of 3 inches each. On chewing, the chewing gum has a pleasant, long-lasting tropical fruit/coconut flavor.

EXAMPLE XVIII

Chewing Gum

100 Parts by weight of chicle are mixed with 18 parts by weight of the flavor prepared in accordance with Example XV. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inch in thickness. The strips are cut into lengths of 3 inches each. On chewing, the chewing gum has a pleasant, very long-lasting tropical fruit/coconut flavor.

EXAMPLE XIX

Toothpaste Formulation

The following separate groups of ingredients are prepared:

| PARTS BY WEIGHT | INGREDIENTS |
|---|---|
| | Group "A" |
| 30.200 | Glycerine |
| 15.325 | Distilled water |
| .100 | Sodium benzoate |
| .125 | Saccharin sodium |
| .400 | Stannous fluoride |
| | Group "B" |
| 12.500 | Calcium carbonate |
| 37.200 | Dicalcium phosphate (dihydrate) |
| | Group "C" |
| 2.000 | Sodium n-lauroyl sarcosinate (foaming agent) |
| | Group "D" |
| 1.200 | Flavor material of Example XV Part B |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour.

The completed paste is then transferred to a three roller mill and then homogenized, and finally tubed.

23

The resulting toothpaste when used in a normal toothbrushing procedure yields a pleasant tropical fruit/coconut flavor of constant strong intensity throughout said procedure (1–1.5 minutes).

EXAMPLE XX

Chewable Vitamin Tablets

The flavor material produced according to the process of Example XV, Part B, is added to a chewable vitamin tablet formulation at a rate of 10 grams per kilogram which chewable vitamin tablet formulation is prepared as follows:

In a Hobart Mixer, the following materials are blended to a homogeneity:

| INGREDIENTS | GRAMS PER 1000 TABLETS |
|---|---|
| Vitamin C (ascorbic acid) as ascorbic acid-sodium ascorbate mixture 1:1 | 70.110 |
| Vitamin B$_1$ (thiamine mononitrate) as ROCOAT ® thiamine mononitrate 33⅓% (Hoffman La Roche) | 4.000 |
| Vitamin B$_2$ (riboflavin) as ROCOAT ® ribflavin 33⅓% | 5.000 |
| Vitamin B$_6$ (pyridoxine hydrochloride) as ROCOAT ® pyridoxine hydrochloride 33⅓% | 4.000 |
| Niacinamide as ROCOAT ® niacinamide 33⅓% | 33.000 |
| Calcium pantothenate | 11.500 |
| Vitamin B$_{12}$ (cyanocobalamin) as Merck 0.1% in gelatin | 3.500 |
| Vitamin E 9di-alpha tocopheryl acetate) as dry Vitamin E acetate 33⅓% Roche | 6.600 |
| d-biotin | 0.144 |
| Flavor of Example XV, Part B | (as indicated above) |
| Certified lake color | 5.000 |
| Sweetener- sodium saccharin | 1.000 |
| Magnesium stearate lubricant | 10.000 |
| Mannitol, q.s. to make | 500.000 |

Preliminary tablets are prepared by slugging with flat faced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong coconut/tropical fruit flavor for a period of 12 minutes.

EXAMPLE XXI

Coconut/Tropical Fruit Flavored Macaroon

A standard almond paste/tropical fruit flavor/coconut macaroon cookie is prepared whereby immediately prior to placing the paste into molds for the purposes of baking, the mix is intimately admixed with one of the hexynyl alkanoates prepared according to Examples II or III or a 50:50 mixture of 3-hexynyl hexanoate and 3-hexynyl butyrate prepared according to Examples II and III at the rates of 20 ppm, 25 ppm, 30 ppm, 50 ppm and 80 ppm. The resulting molded pastes are baked to yield macaroon/tropical fruit cookies. The toasted macaroon/tropical fruit cookies are much more natural coconut-like and tropical fruit-like than those produced without the hexynyl alkanoates prepared according to Examples II or III and are preferred by a four member bench panel of experts.

The coconut/tropical fruit macaroon cookies are of the type distributed by Drake Bakeries, Division of Borden Inc., of Columbus, Ohio, having the ingredients:

Corn syrup;
Coconut;
Sucrose;
Egg whites;
Corn starch;
Sodium chloride;
Sodium carbonate;
Water;
Sodium acid pyrophosphate;
Monocalcium phosphate; and
Calcium sulfate
weighing 0.56 ozs. each.

EXAMPLE XXII

Tropical Fruit Nectar Flavors

Part A

At the rate of 2 ppm, 3-hexynyl hexanoate having the structure:

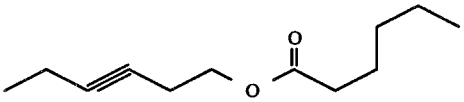

is added to Goya Nectar De Papaya, manufactured by Goya De Puerto Rico Inc. of Bayamon, Puerto Rico 00619. The 3-hexynyl hexanoate imparts to the Goya Papaya Nectar a much more natural-like papaya flavor.

Part B

At the rate of 2 ppm, 3-hexynyl hexanoate having the structure:

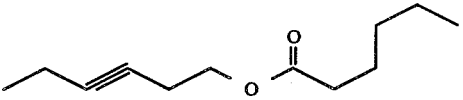

is added to Nectar De Guanabana, manufactured by Goya De Puerto Rico Inc. of Bayamon, Puerto Rico 00619. The 3-hexynyl hexanoate imparts to the Nectar De Guanabana a much more natural-like guanabana flavor.

Part C

At the rate of 2 ppm, 3-hexynyl hexanoate having the structure:

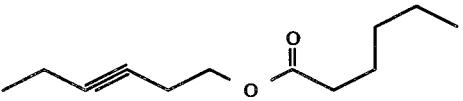

is added to Nectar De Guayaba, manufactured by Goya De Puerto Rico Inc. of Bayamon, Puerto Rico 00619. The 3-hexynyl hexanoate imparts to the Nectar De Guayaba a much more natural-like guayaba flavor.

Part D

At the rate of 2 ppm, 3-hexynyl hexanoate having the structure:

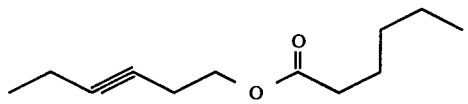

is added to Nectar De Mango, manufactured by Goya De Puerto Rico Inc. of Bayamon, Puerto Rico 00619. The 3-hexynyl hexanoate imparts to the Nectar De Mango a much more natural-like mango flavor.

What is claimed is:

1. A hexynyl alkanoate defined according to the structure:

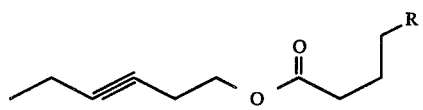

wherein R represents hydrogen or ethyl.

2. The hexynyl alkanoate of claim 1 wherein R is hydrogen.

3. The hexynyl alkanoate of claim 1 wherein R is ethyl.

4. A process for augmenting or enhancing the aroma or taste of a consumable material selected from the group consisting of perfume compositions, colognes, and perfumed articles, comprising the step of adding to said consumable material an aroma augmenting or enhancing quantity of at least one compound defined according to claim 1.

5. The process of claim 4 wherein the consumable material is a perfume composition, cologne or perfumed polymer.

6. The process of claim 4 wherein the consumable material is a perfumed article and the perfumed article is a solid or liquid anionic, cationic, nonionic or zwitterionic detergent.

7. The process of claim 4 wherein the consumable material is a perfumed article and the perfumed article is a fabric softener composition or a dryer-added fabric softener article.

8. The process of claim 4 wherein the consumable material is a perfume composition, cologne or perfumed polymer and R represents ethyl.

* * * * *